United States Patent [19]
Faller

[11] Patent Number: 5,575,807
[45] Date of Patent: Nov. 19, 1996

[54] MEDICAL DEVICE POWER SUPPLY WITH AC DISCONNECT ALARM AND METHOD OF SUPPLYING POWER TO A MEDICAL DEVICE

[75] Inventor: Frederick W. Faller, Burlington, Mass.

[73] Assignee: ZMD Corporation, Wilmington, Del.

[21] Appl. No.: 353,389

[22] Filed: Dec. 2, 1994

Related U.S. Application Data

[63] Continuation-in-part of Ser. No. 258,238, Jun. 10, 1994, Pat. No. 5,470,343.

[51] Int. Cl.$^6$ ................................................ A61N 1/39
[52] U.S. Cl. ........................................................ 607/5
[58] Field of Search ................................ 607/5, 33, 61; 340/568, 635, 652, 654, 656

[56] References Cited

U.S. PATENT DOCUMENTS

| | | | |
|---|---|---|---|
| 3,758,839 | 9/1973 | Medlar | 320/32 |
| 3,862,636 | 1/1975 | Bell et al. | 128/419 D |
| 3,865,101 | 2/1975 | Saper et al. | 128/2.06 R |
| 4,019,111 | 4/1977 | Bennefeld | 320/23 |
| 4,077,413 | 3/1978 | Partridge | 128/419 D |
| 4,080,558 | 3/1978 | Sullivan | 320/39 |
| 4,119,903 | 10/1978 | Pirkle | 320/1 |
| 4,233,659 | 11/1980 | Pirkle | 363/134 |
| 4,413,228 | 11/1983 | Turner, Jr. | 340/652 |
| 4,590,943 | 5/1986 | Paull et al. | 128/419 |
| 4,639,656 | 1/1987 | Mukai | 320/22 |
| 4,653,474 | 3/1987 | Reithler | 128/1 R |
| 4,952,861 | 8/1990 | Horn | 320/23 |
| 5,034,728 | 7/1991 | Taylor | 340/656 |
| 5,088,489 | 2/1992 | Lerman | 128/419 |
| 5,089,763 | 2/1992 | Van Der Linden et al. | 320/20 |
| 5,105,182 | 4/1992 | Shindo | 340/654 |
| 5,163,428 | 11/1992 | Pless | 128/419 D |
| 5,224,870 | 7/1993 | Weaver et al. | 439/157 |
| 5,233,659 | 8/1993 | Ahlberg | 381/30 |
| 5,237,259 | 8/1993 | Sanpei | 320/23 |
| 5,243,975 | 9/1993 | Alferness et al. | 607/7 |
| 5,321,392 | 6/1994 | Skakoon et al. | 340/635 |

Primary Examiner—William E. Kamm
Attorney, Agent, or Firm—Fish & Richardson P.C.

[57] ABSTRACT

A power supply for supplying power from an external power source to a medical device for charging a battery of the medical device and operating the medical device includes an external power connection for bringing external power into the power supply, a power module having a power circuit that converts power from the external power source to a form useable by the medical device, monitoring circuitry for monitoring the external power connection to determine whether the external power connection is connected to a source of external power, and alarm circuitry for generating an alarm when the monitoring circuitry determines that the external power connection is not connected to a source of external power.

21 Claims, 7 Drawing Sheets

MEDICAL DEVICE POWER SUPPLY WITH AC DISCONNECT ALARM AND METHOD OF SUPPLYING POWER TO A MEDICAL DEVICE

CROSS-REFERENCE TO RELATED APPLICATIONS

This application is a continuation-in-part of co-pending U.S. patent application Ser. No. 08/258,238, entitled "DETACHABLE CONTROLLED CURRENT/VOLTAGE POWER SUPPLY", which was filed on Jun. 10, 1994, now U.S. Pat. No. 5,470,343, and is hereby incorporated by reference.

BACKGROUND OF THE INVENTION

The invention relates to power supplies, particularly power supplies for charging the batteries of portable defibrillators.

Portable defibrillators, such as the PD 1400 Series Products available from Zoll Medical Corporation of Burlington, Mass., deliver high energy shocks to a patient's chest for defibrillation. Typically, portable defibrillators employ batteries (e.g., lead acid batteries) to store power for generating such shocks. Eventually, the power stored in the batteries is used, and the batteries must be recharged from a source of AC power.

AC power supplies, which convert AC power to DC power, have been used for operating a portable defibrillator and for recharging the batteries in the portable defibrillator. Approaches to using AC power supplies include: building an AC power supply into the portable defibrillator; supplying an AC power supply in a separate box that includes a cord for attachment to the portable defibrillator; attaching the portable defibrillator into a "docking station" that contains an AC power supply (so that the combination of the docking station and the portable defibrillator is not itself portable); and removing the batteries from the portable defibrillator for charging in a separate AC powered unit (in which case the AC powered unit does not power the defibrillator).

SUMMARY OF THE INVENTION

The invention provides a power supply that produces an alarm signal when the power supply is not connected to a source of AC power and that is intended for use with a medical device such as a portable defibrillator. In the emergency situations in which a portable defibrillator is typically employed, it is vital that a the defibrillator be properly charged and available for use at a moment's notice. By producing an alarm when it is not connected to a source of AC power, the power supply ensures that a battery of the defibrillator will not inadvertently be left uncharged.

Typically, the power supply produces the alarm when the power supply needs to be connected to a source of AC power, which occurs when the power supply is not connected to a source of AC power and there is a battery to be charged (i.e., the power supply is connected to the portable defibrillator and there is a battery present in the defibrillator). This ensures that the power supply will not signal a user to plug in the power supply unnecessarily, such as when the portable defibrillator does not include a battery to be charged. Similarly, to avoid interruptions during emergency situations, the power supply only produces the alarm signal when the portable defibrillator is turned off.

The alarm signal may include a visible signal such as a flashing light emitting diode (LED) that warns a user who is observing the power supply that the power supply needs to be connected to a source of AC power. The alarm signal may also include an audible signal to warn a user who is not observing the power supply. For example, when it is desired to charge the portable defibrillator while the defibrillator is in storage, the audible signal would provide a warning to user who was not in the storage area that, for example, the power supply had been inadvertently unplugged. The power supply may be programmed to only activate the alarm upon the expiration of a predetermined delay period.

In one aspect, generally, the invention includes a power supply for supplying power from an external power source to a medical device for charging a battery of the medical device and operating the medical device. The power supply includes an external power connection for bringing external power into the power supply, a power module having a power circuit that converts power from the external power source to a form useable by the medical device, monitoring circuitry for monitoring the external power connection to determine whether the external power connection is connected to a source of external power, and alarm circuitry for generating an alarm when the monitoring circuitry determines that the external power connection is not connected to a source of external power.

When the medical device includes a removable battery, the monitoring circuitry may also include circuitry for determining whether the battery is present, and the alarm circuitry may be operable to generate the alarm only when the monitoring circuitry determines that the external power connection is not connected to a source of external power and that the battery is present. This circuitry prevents unnecessary activation of the alarm when a battery is not present to be charged.

The monitoring circuitry may also include circuitry for determining whether the device is turned on. If so, the alarm circuitry is operable to generate the alarm when the monitoring circuitry determines that the external power connection is not connected to a source of external power, that a battery is present, and that the device is not turned on. As discussed above, this circuitry prevents unnecessary activation of the alarm when the device is in use.

Finally, when the power supply is detachable from the device, the monitoring circuitry may include circuitry for determining whether the power supply is connected to the device. In this case, the alarm circuitry will be operable to generate the alarm either when the monitoring circuitry determines that the power supply is connected to the device and that one or more of the other conditions specified above are satisfied. Like the circuitry that determines whether a battery is present, this circuit prevents unnecessary activation of the alarm when the battery is not present and connection to AC power would serve no purpose.

In preferred embodiments, the device is a portable defibrillator and the power module has a power circuit that converts power from the external power source to a form useable by the portable defibrillator. In some cases, circuitry for determining whether the portable defibrillator is turned on may include circuitry that detects a signal produced by the portable defibrillator when the portable defibrillator is turned on.

When the alarm circuitry includes circuitry that produces an audible alarm, the alarm circuitry may be configurable to disable the audible alarm. When the alarm circuitry also includes circuitry that produces a visible alarm, the power supply may be configurable to disable the audible alarm without disabling the visible alarm. Since the audible alarm may be inappropriate in some circumstances, this selective disabling is beneficial in that it still retains many of the benefits of the alarm.

The alarm circuitry may also be configurable to wait for the expiration of a predetermined, selectable delay period after the monitoring circuitry determines that the external power connection is not connected to a source of external power and, perhaps, other conditions are satisfied before generating the alarm.

The invention also features a method of supplying power from an external power source to a battery-powered medical device for charging a battery of the medical device and operating the medical device. The method includes bringing external power into a power supply from an external power source through an external power connection, converting power from the external power source to a form useable by the medical device, monitoring the external power connection to determine whether the external power connection is connected to the source of external power, and generating an alarm when the external power connection is not connected to the source of external power. The method also may include implementing other features of the power supply discussed above.

Other features and advantages of the invention will be apparent from the following description of the preferred embodiments and from the claims.

DESCRIPTION OF THE PREFERRED EMBODIMENTS

Figure 1:
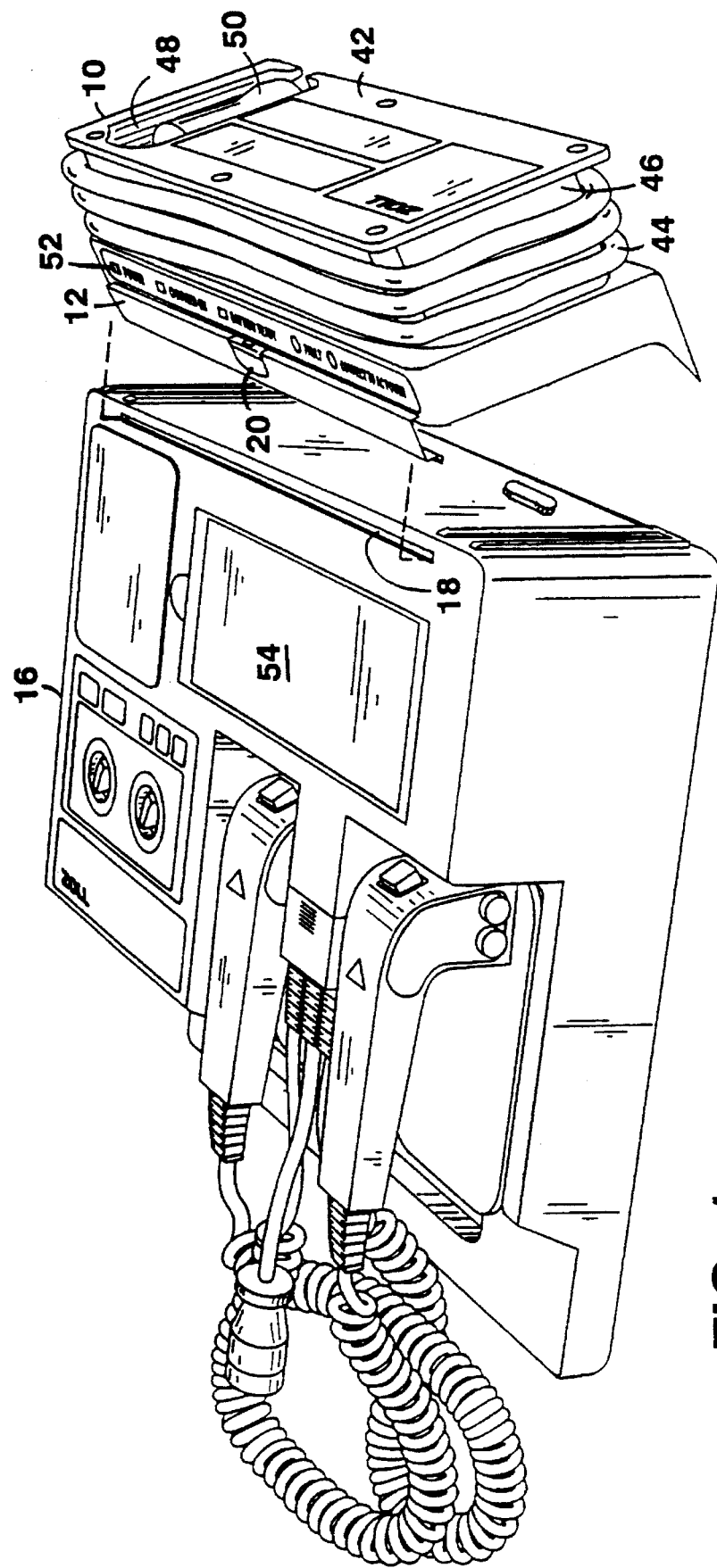
FIG. 1 is a perspective view of a detachable power supply and a portable defibrillator.
Figure 2:
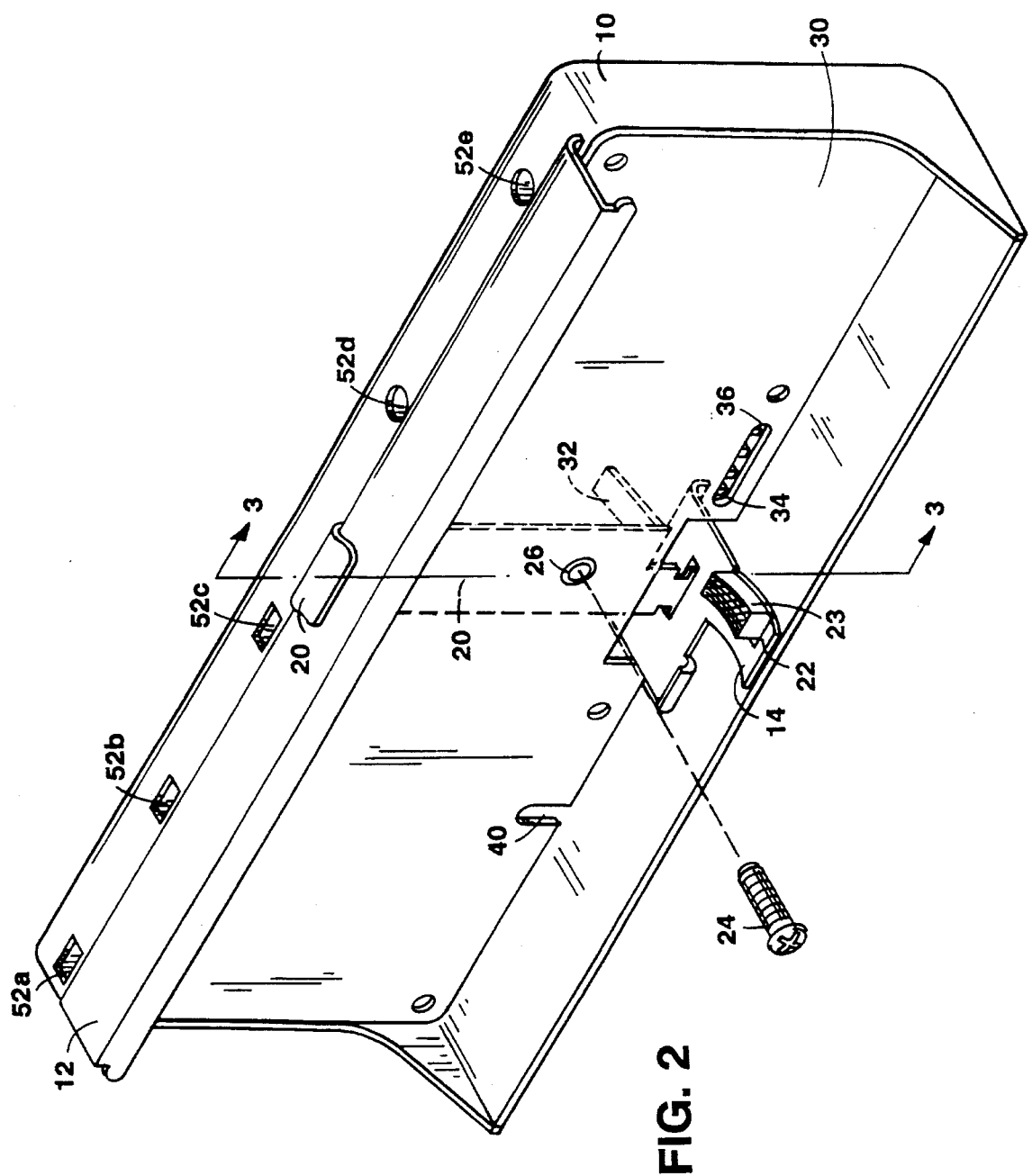
FIG. 2 is a perspective view of the power supply of FIG. 1.

FIGS. 1 and 2 show a portable defibrillator 16 and detachable power supply 10. The detachable power supply 10 includes a continuous and elongated hook member 12 located near the top of the power supply and a latch 14 (see FIG. 2) located near the bottom of the power supply for attachment to the portable defibrillator 16. Power supply 10 is attached by placing hook member 12 in a slot 18 in the upper housing of the defibrillator and engaging the latch. The power supply is detached by pressing a latch release 20 to disengage the latch.

Specifically, the top of the power supply is held in place against the defibrillator by the engagement of hook member 12 with slot 18. The power supply is swung into place so that a portion 22 of latch 14 secures the bottom of the power supply to a portion 23 of the lower housing of the defibrillator. The power supply is released by pressing on latch release 20, which protrudes through the top edge of the power supply. Thus, the power supply can be attached to and released from the defibrillator with a single hand, and without manipulating the latch.

Latch 14 is a piece of stamped sheet metal which, when attached, links the housing of the power supply to the housing of the defibrillator. The latch, which can be disengaged only when unstressed, is designed so that increased pull on the housings to separate them makes the latch harder to disengage.

Figure 3:
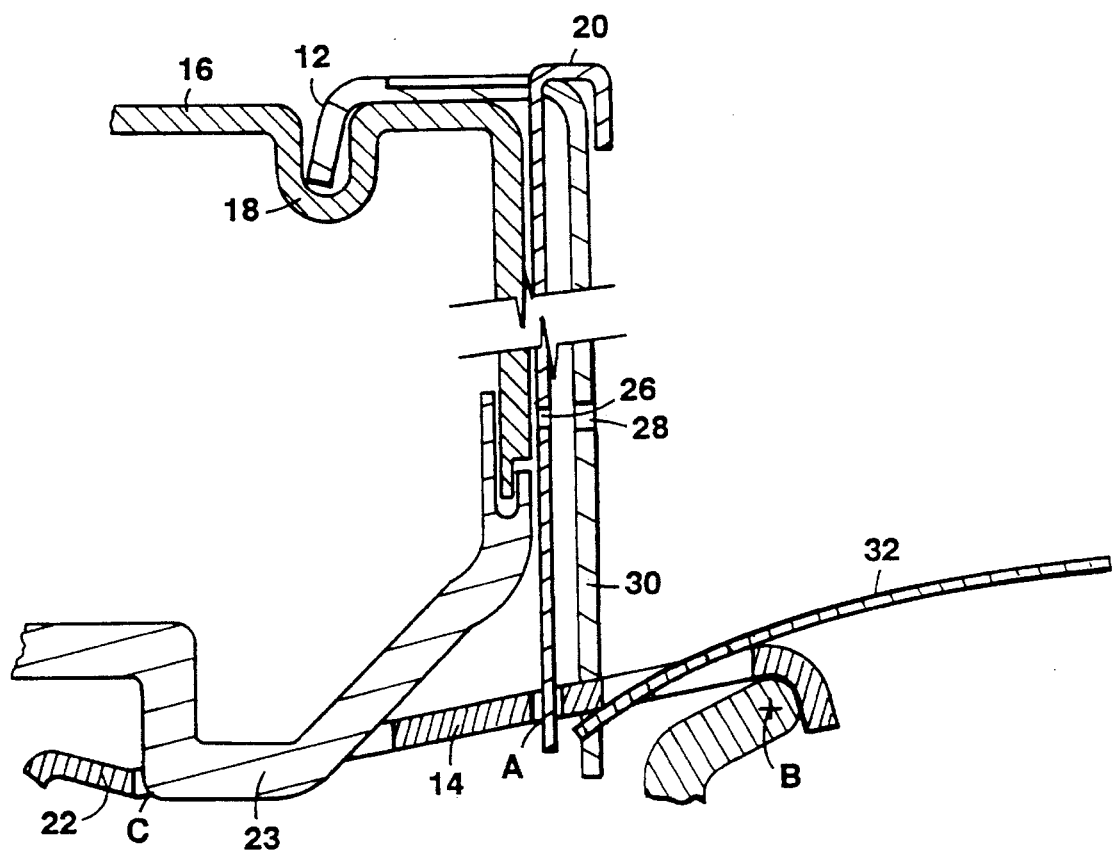
FIG. 3 is a cutaway side view of the power supply of FIG. 2 taken along line 3—3 of FIG. 2.

Referring also to FIG. 3, latch 14 is locked by putting a screw 24 (FIG. 2) through a hole 26 in latch release 20 and into a threaded insert 28 in a metal cover plate 30 of the power supply. When screw 24 is in place, the position of the latch release is fixed, and the latch pivots around its engagement with the latch release at point A. In this configuration, the power supply can still be attached to the defibrillator, but cannot be detached without using a tool. The latch is disengaged, and the power supply is detached, by taking a tool (e.g., a screwdriver) and pushing on the back edge of the latch (near point B) so that the latch disengages at point C. (The power supply cannot be detached by removing screw 24 because, when the power supply is attached to the defibrillator, screw 24 is located between the power supply and the defibrillator.)

When screw 24 is not in place, latch release 20 is free to move up and down, and the latch pivots around its engagement at point B with the housing of power supply 10. The latch release is biased upward by pressure exerted on the latch by a spring 32 located within the power supply. When the latch release is pressed downward, pivoting of the latch about point B causes the latch to disengage at point C. Once the latch is disengaged, the power supply is removed by swinging the bottom of the power supply away from the defibrillator, and removing the hook member from the slot.

Power supply 10 makes electrical connection with portable defibrillator 16 through pins 34a–34e (see FIG. 4), referred to collectively as pins 34, located within a port 36. Pins 34 fit within a socket 38 on the defibrillator. For safety reasons, power pin 34a is only active when the power supply is attached to the defibrillator. When the power supply is attached to the defibrillator, an extension (not shown) on the defibrillator closes two series interlock switches 39 (see FIG. 4) located within a recess 40 on the power supply, and thereby activates power pin 34a. Interlock switches 39 isolate power pin 34a from a power module 58 (see FIG. 4) of the power supply when the power supply is detached from the defibrillator.

Power supply 10 also includes a ruggedized base 42 and an eight-foot, integral cord 44. For storage of integral cord 44, base 42 includes an indentation 46 around its periphery and a recess 48 at its back end. Indentation 46 and recess 48 are configured so that integral cord 44 can be wrapped around indentation 46 and a plug 50 of integral cord 44 can be secured in recess 48. Recess 48 is configured so that plug 50 is flush with the surface of base 42 when stored within recess 48, which allows the defibrillator to stand on end even when the power supply is attached and plug 50 is secured in recess 48.

Another external feature of the power supply is a set of five indicator LEDs (light emitting diodes) 52a–52e, referred to collectively as indicator LEDs 52, located along the top of the power supply. Yellow indicator LED 52a is lit when the power supply is connected to a source of AC power and capable of operating the defibrillator and/or charging a battery 54 of the defibrillator. Yellow indicator LED 52b is lit when battery 54 is installed in the defibrillator and is receiving a charge. Green indicator LED 52c is lit when battery 54 is fully charged and therefore ready for use. Yellow indicator LED 52d is lit when a fault is detected in the power supply or battery 54. Finally, flashing yellow indicator LED 52e is activated when the power supply needs to be connected to a source of AC power.

The power supply is 10.5 inches (26.7 cm) wide, 4 inches (10.2 cm) high, and 2.5 inches (6.4 cm) deep, and weighs 3.1 pounds (1.4 kg). While the housing of the power supply is made typically from a molded polymer, other materials such as, for example, coated magnesium could also be used. The power supply is configurable to operate with AC input voltages of 90–135 (110) or 190–265 (220) volts at frequencies of 50 or 60 Hz, and also works with a 165 volt square wave converter, such as is commonly available in ambulances. The power supply powers the defibrillator regardless of whether a battery is present in the defibrillator.

Figure 4:
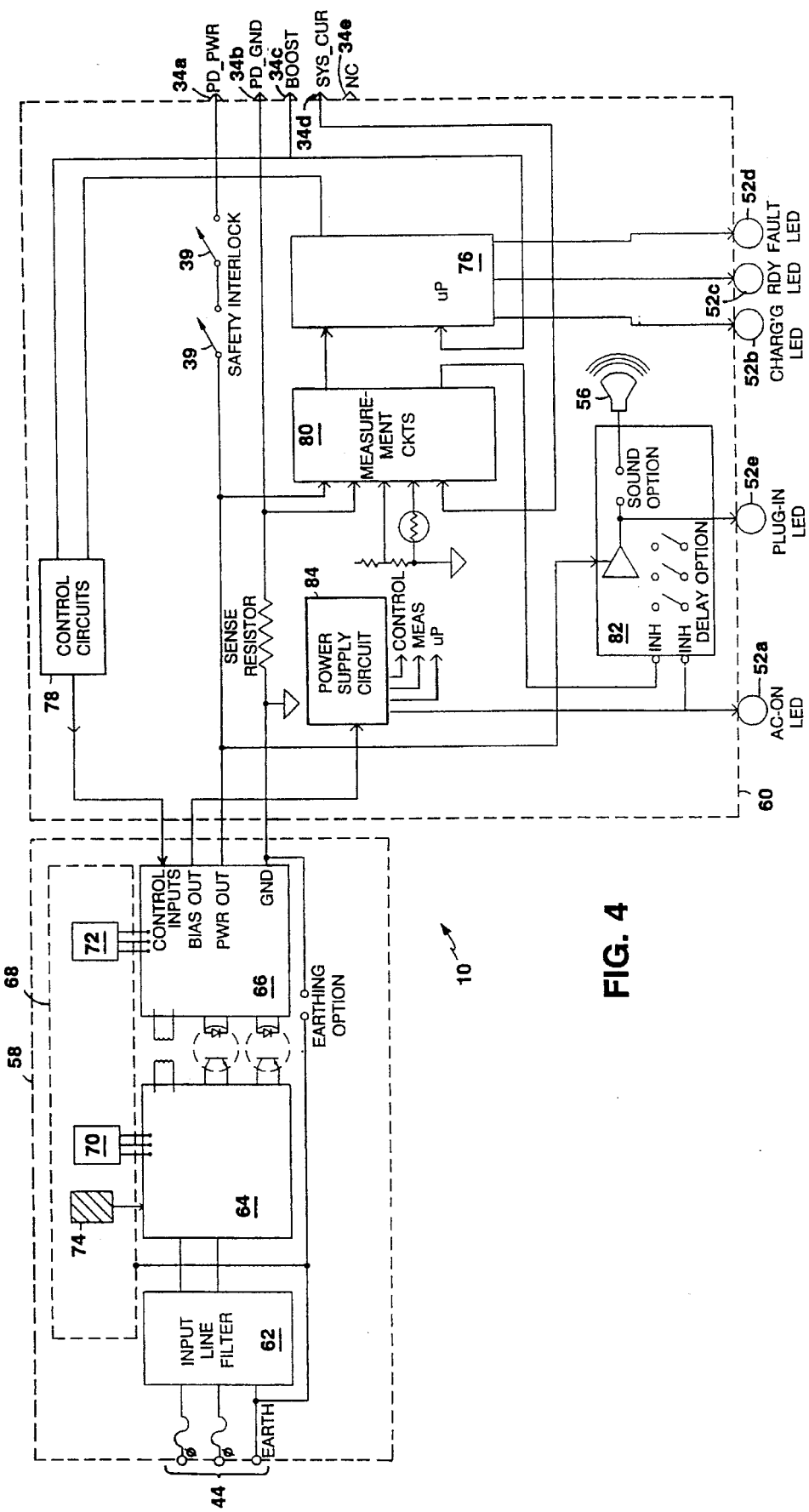
FIG. 4 is a block diagram of the power supply of FIG. 2.

Referring to FIG. 4, power supply 10 includes a power module 58 and a control module 60. Power module 58 includes an input line filter 62 that is connected to integral cord 44 and shapes the input voltage therefrom, a voltage selector 64 that allows configurable selection between input voltages of 110 volts and 220 volts, and an output circuit 66 that, in response to control inputs, produces either a controlled voltage or a controlled current. Power module 58 also includes a heat sink 68 connected to heat producing components 70, 72 of, respectively voltage selector 64 and output circuit 66. A thermal shutdown device 74 that shuts down power module 58 in response to excessive heat is also connected to heat sink 68.

Output circuit 66 operates in either a controlled voltage charging mode, in which it delivers a generally constant output voltage of about 11.75 volts at up to 3.5 amps; a low voltage charging mode, in which it delivers a generally constant output voltage of about 10.75 volts at up to 10.0 amps; a controlled current charging mode, in which it delivers a generally constant output current of up to 0.835 amps at a voltage of up to 16.5 volts, and a battery search mode, in which it delivers a generally constant output voltage of 15 volts at up to 0.3 amps. Though the controlled voltages or currents are generally constant, some variation is allowed. For example, in the preferred embodiment, the 11.75 volt output voltage in the controlled voltage charging mode can vary between 11.5 and 12 volts, while the 10.75 volt output voltage in the low voltage charging mode can vary between 10.3 and 10.9 volts. Similarly, the output current in the controlled current charging mode can vary between 0.735 and 0.935 amps.

Figure 5:
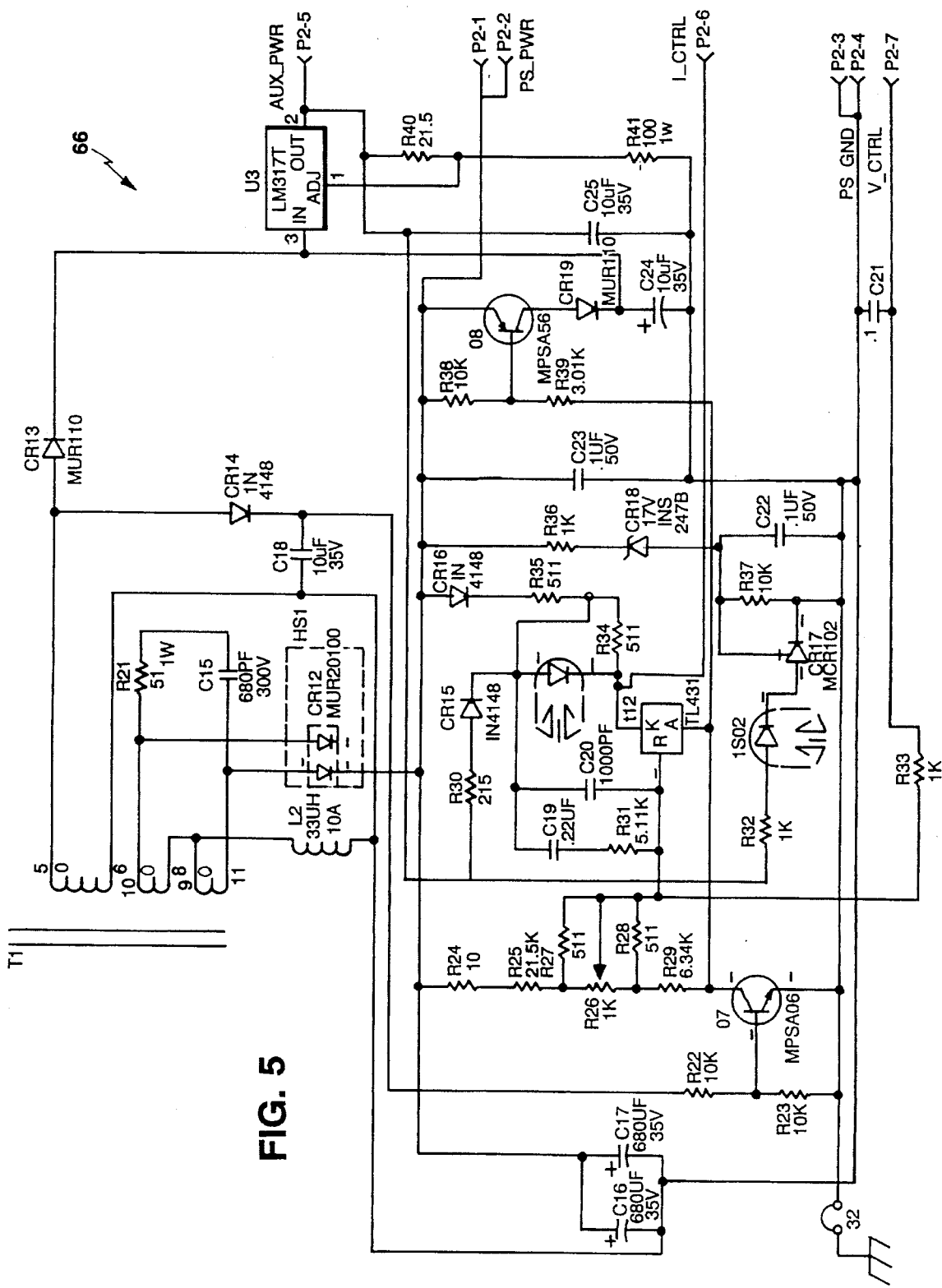
FIG. 5 is a circuit diagram of an output circuit of a power module of the power supply of FIG. 2.

Referring to FIG. 5, output circuit 66 rectifies the alternating voltage and current from the transformer secondary (T1) through the two legs of a center tap 100 V Schottky diode (CR12). During the dead time between power cycles, both diode legs are forward biased and the magnetizing current in the transformer appears as an offset between the two currents. Leakage spikes from the transformer are snubbed to a safe reverse voltage level by R21 and C15.

The rectified transformer voltage appears across an output filter that includes a 33 µH inductor (L2) and two 680 µF capacitors (C16 and C17). During power transfer, the rectified transformer voltage energizes the inductor and provides output current to the load. During dead time, the inductor provides the energy delivered to the load. The inductor current is continuously flowing for normal operating loads greater than 1.6 A.

The output voltage (PS_PWR) of output circuit 66 is sensed by a set of resistors (R24 through R29) that includes a potentiometer (R26) for factory adjustment. A tap off these resistors, which has a nominal value of 2.5 volts, connects to a reference pin (R) of a band gap device (U2). This connection functions as the negative input of an error amplifier of a feedback control loop. This loop is stabilized by compensation provided by C19, C20, and R31.

The output voltage of output circuit 66 is regulated to hold the reference pin of the band gap device (U2) sufficiently above 2.5 V to cause the cathode (K) of the band gap device to sink a required current through the diode of the optocoupler IS01. The current required through the optocoupler diode is determined by the current required through the transistor of IS01 (which is located in voltage selector 64). The current through the transistor of IS01 sets the duty cycle of the output of voltage selector 64 to a value that allows output circuit 66 to produce a desired output voltage. Bias current for the optocoupler diode is provided from the output of output circuit 66 through R30 and CR15, and from the auxiliary output (AUX_PWR) of output circuit 66 through R35 and CR16. Bias current is redundantly supplied by the auxiliary output for fault condition operation. In normal operation, the auxiliary output is set between 6.5 volts and 7.5 volts, and diode CR16 is back-biased so that noise from the auxiliary output is not coupled into the control circuit.

The control circuitry connected to the output of output circuit 66 draws approximately 12 mA. Because the product application requires the output to be connected directly across a battery, the battery would be drained by this control circuitry if line power were not provided to output circuit 66. To avoid draining the battery, the control circuitry is switched on and off through an NPN transistor (Q7). current to turn on this transistor is provided from a tap winding off of the transformer and a resistor network (R22 and R23).

Output circuit 66 is set so that its output voltage (PS_PWR) does not exceed 17.6 volts. If the voltage exceeds this level, an over voltage protection circuit is activated. This circuit includes a 17 volt zener diode (CR18) that, when the output voltage exceeds 17.6 volts, conducts enough to drive the gate of an SCR (CR17) above threshold. When the gate of the SCR is driven above threshold, current is driven through the diode of optocoupler IS02 through R32 from the auxiliary output. Current flowing through the diode of optocoupler IS02 inhibits the production of power by voltage selector 64 until the output voltage drops to the point where the IS02 diode no longer conducts. At that point, voltage selector 64 is again able to produce power.

The auxiliary output (AUX_PWR) is set by an LM317T adjustable three terminal regulator (U3). In normal operation, input power to this device is provided by a tap off of the transformer. However, the auxiliary must be kept turned on during transitions for which the power supply is back driven by a battery. In those cases, auxiliary power is provided from the battery through Q8 and CR19. Q8 has a particular functional window within which it is operational. When the power supply is not providing any power, Q7 is off, which turns Q8 off and ensures that the battery is not drained. When the power supply is providing normal operating power, CR19 is back biased by the tap winding.

Output circuit 66 interfaces with control module 60 through an eight conductor cable harness terminated on each end with an eight position crimp terminal housing which mates with a PCB mounted connector. The pin assignment at the interface is as follows:

| Pin Number | Function | Title |
|---|---|---|
| 1 | Output (+) | PS_PWR |
| 2 | Output (+) | PS_PWR |
| 2 | Output (−) | PS_GND |
| 3 | Output (−) | PS_GND |
| 5 | Auxiliary (+) | AUX_PWR |
| 6 | Current Control | I_CTRL |
| 7 | Voltage Control | V_CTRL |
| 8 | No Connection | N/A |

Two conductors each are provided for both the output power and output ground to minimize voltage drops under heavy load. The output is regulated on the power supply and therefore does not compensate for drops through the connector.

The output voltage is nominally set to 10.75 volts. When required by the system, the voltage setting is changed by connecting the voltage control line (V_CTRL) to a fixed voltage (5 volts or 0 volts) through one of a set of fixed resistances in control module 60. This control signal changes the voltage/impedance characteristics of the reference pin of U2. Through the possible control signals, control module 60 can set the voltage within a range of 10.75 volts to 16.25 volts. The control line is protected from electrostatic discharge with a series, one kiloohm resistor (R33).

The output current is sensed by control module 60. This current sense signal is used to provide over current protection and current control as required by the system. The control signal to the power supply is in the form of a sink current through the diode of optocoupler IS01. When active, this control signal overrides the voltage control because the cathode (K) of U2 enters an open circuit mode when the output voltage causes the U2 reference voltage to fall below 2.5 V.

To provide over current protection while the output collapses, the diode of IS01 receives current from the auxiliary output in addition to the main output. Control module 60 thus can drive the main output down to zero volts in severe over current conditions.

Referring again to FIG. 4, control module 60 includes a microprocessor 76 that has overall control of the power supply. Microprocessor 76 is an 87C752 processor running at 6.144 MHz with two kilobytes of internal ROM and 64 bytes of internal RAM. Microprocessor 76 includes a six bit I/O port and two eight bit I/O ports.

A control circuit 78 responds to signals from microprocessor 76 and a BOOST signal from the defibrillator to supply control signals to output circuit 66. The defibrillator turns on the BOOST signal when the defibrillator is producing a pace pulse or otherwise needs to receive defibrillation charge energy. In control module 60, the BOOST signal, which is received on pin 34c, is input into a comparator that produces a digital (high/low) output. This digital output is supplied to microprocessor 76 for control of the power supply and, in particular, output circuit 66. In addition, to ensure that the power supply immediately responds to the BOOST signal, the digital output is supplied directly to control circuit 78.

Measurement circuits 80 monitor the output voltage of output circuit 66, the current supplied to battery 54, and other signals, to provide information that allows microprocessor 76 to determine the charge status of battery 54.

Other components of control module 60 include AC disconnect alarm circuitry 82 that activates flashing indicator LED 52e and a beeper 56 when the power supply should be connected to a source of AC power, and a power supply circuit 84 that supplies operating power to microprocessor 76, control circuits 78, measurement circuits 80 and AC disconnect alarm circuitry 82. Power supply circuit 84 is powered by the auxiliary output (AUX_PWR) of output circuit 66.

Generally, microprocessor 76 configures the power supply to deliver a controlled voltage when the defibrillator is turned on, and either a controlled voltage or a controlled current when the defibrillator is turned off. Use of a controlled current reduces the time required to charge a battery of the defibrillator from about sixteen hours to about three hours.

Figure 6:
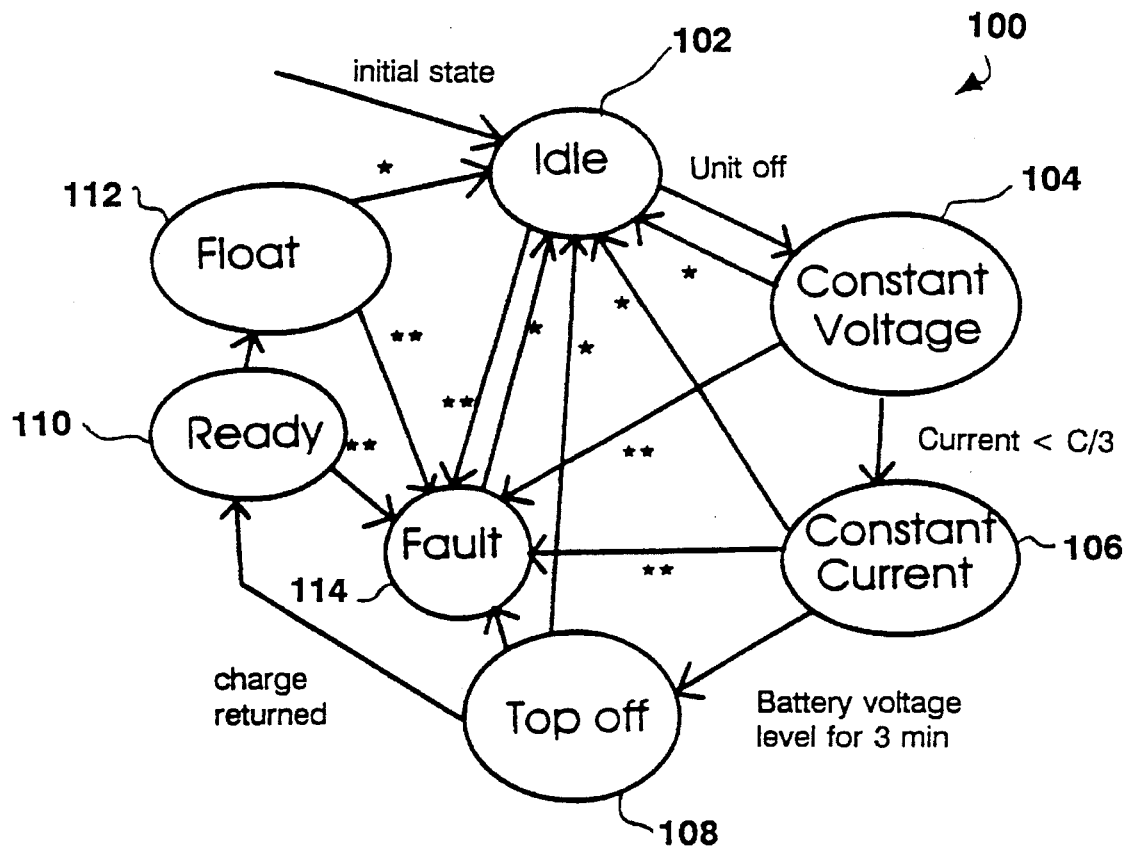
FIG. 6 is a state diagram for a charging procedure implemented by the power supply of FIG. 2.

More specifically, as illustrated in FIG. 6, microprocessor 76 controls delivery of power according to a procedure 100 that microprocessor 76 invokes approximately once every 10 milliseconds. In implementing procedure 100, processor 76 monitors several characteristics of the power supply and the defibrillator, including the voltage level of battery 54, the current supplied to the defibrillator, the on/off state of the defibrillator, and the presence or absence of battery 54 and/or the BOOST signal from the defibrillator. Microprocessor 76 determines the on/off state of the defibrillator from a signal received on pin 34d.

At initialization, the power supply operates in an IDLE state 102. In IDLE state 102, output circuit 66 operates in low voltage mode if the power supply is connected to the defibrillator and the BOOST signal from the defibrillator is on, and otherwise operates in controlled voltage mode.

The power supply transitions from IDLE state 102 to a CONSTANT VOLTAGE state 104 when the power supply is connected to the defibrillator, the defibrillator is turned off, battery 54 is present, and the BOOST signal is off. In making the transition, microprocessor 76 resets an integrated total charge value.

In IDLE state 102, if portable defibrillator is turned off, microprocessor 76 determines whether battery 54 is present by implementing a battery search procedure. First, microprocessor 76 places output circuit 66 in battery search mode. After waiting for 50 milliseconds to allow the output voltage to reflect the change in the charging mode, microprocessor 76 measures the current being delivered to the defibrillator. If this current exceeds 100 milliamps, the microprocessor 76 determines that battery 54 is present. Otherwise, microprocessor 76 determines that battery 54 is not present. Thereafter, microprocessor 76 places output circuit 76 in controlled voltage mode and waits for 50 milliseconds to allow the output voltage to reflect the change in the charging mode. Typically, microprocessor 76 activates the battery search mode once every 500 milliseconds.

In CONSTANT VOLTAGE state 104, output circuit 66 operates in the controlled voltage mode. During charging, microprocessor 76 periodically adds a measure of the current being supplied to the defibrillator to the integrated total charge value, and thereby maintains a measure of the total charge being supplied to battery 54.

The power supply transitions from CONSTANT VOLTAGE state 104 to a CONSTANT CURRENT state 106 when the average current supplied to the defibrillator is less than or equal to a predetermined controlled current charging rate. The power supply returns to IDLE state 102 from CONSTANT VOLTAGE state 104 when the power supply is disconnected from the defibrillator or the defibrillator is turned on. (If battery 54 is not present, this will cause the current to fall below the controlled current charging rate.)

In CONSTANT CURRENT state 106, output circuit 66 operates in the controlled current mode and supplies current at the controlled current charging rate. Microprocessor 76 continues to periodically add the current being supplied to the defibrillator to the integrated total charge value. The power supply transitions from CONSTANT CURRENT state 106 to a TOP OFF state 108 when the average battery voltage remains level for three minutes, or begins to drop. The power supply transitions from CONSTANT CURRENT state 106 to IDLE state 102 when the power supply is disconnected from the defibrillator, the defibrillator is turned on, or battery 54 is not present. In CONSTANT CURRENT state 106, microprocessor 76 determines that battery 54 is not present if the measured battery voltage exceeds 15.5 volts.

In TOP OFF state 108, output circuit 66 continues to operate in the controlled current mode and supplies current at the controlled current charging rate. The power supply transitions from TOP OFF state 108 to a READY state 110 when a time period equal to the integrated total charge value divided by sixteen elapses. The power supply transitions from TOP OFF state 108 to IDLE state 102 when the power supply is disconnected from the defibrillator or the defibrillator is turned on.

In READY state 110, output circuit 66 operates in the controlled voltage mode, and microprocessor 76 activates LED 52c to indicate that battery 54 is fully charged. After LED 52c is activated, the power supply transitions to a FLOAT state 112.

In FLOAT state 112, output circuit 66 operates in the controlled voltage mode. The power supply transitions from FLOAT state 112 to IDLE state 102 when the power supply is disconnected from the defibrillator, the defibrillator is turned on, or battery 54 is not present. As in IDLE state 102, microprocessor 76 determines whether battery 54 is present by switching output circuit 76 to the battery search mode.

Finally, if at any time during charging microprocessor 76 detects a fault in the power supply, microprocessor 76 causes the power supply to transition to a FAULT state 114. In FAULT state 114, output circuit operates in low voltage mode if the BOOST signal is on, and otherwise operates in controlled voltage mode. To indicate the presence of a fault, microprocessor 76 turns on LED 52d and, if LED 52c is on, turns off LED 52c (microprocessor 76 also turns off LED 52c in IDLE state 102). The power supply remains in FAULT state 114 until the fault is corrected, at which point the power supply transitions to IDLE state 102.

Referring again to FIG. 4, an AC disconnect alarm, which is implemented by AC disconnect alarm circuitry 82, is activated when the power supply should be connected to a source of AC power. In particular, the AC disconnect alarm is activated when: (1) the power supply is not connected to a source of AC power, (2) the power supply is attached to the defibrillator, (3) the defibrillator is not activated and (4) the battery is in place. In addition to activating flashing yellow indicator LED 52e, the AC disconnect alarm produces an audible signal via beeper 56. AC disconnect alarm circuitry 82 can be adjusted so that the alarm is produced only upon expiration of a predetermined delay period (e.g., after the power supply has needed to be, and has not been, connected to a source of AC power for ten minutes). AC disconnect alarm circuitry 82 also can be adjusted to disable the audible signal or to disable both the visible and audible alarms.

Figure 7:
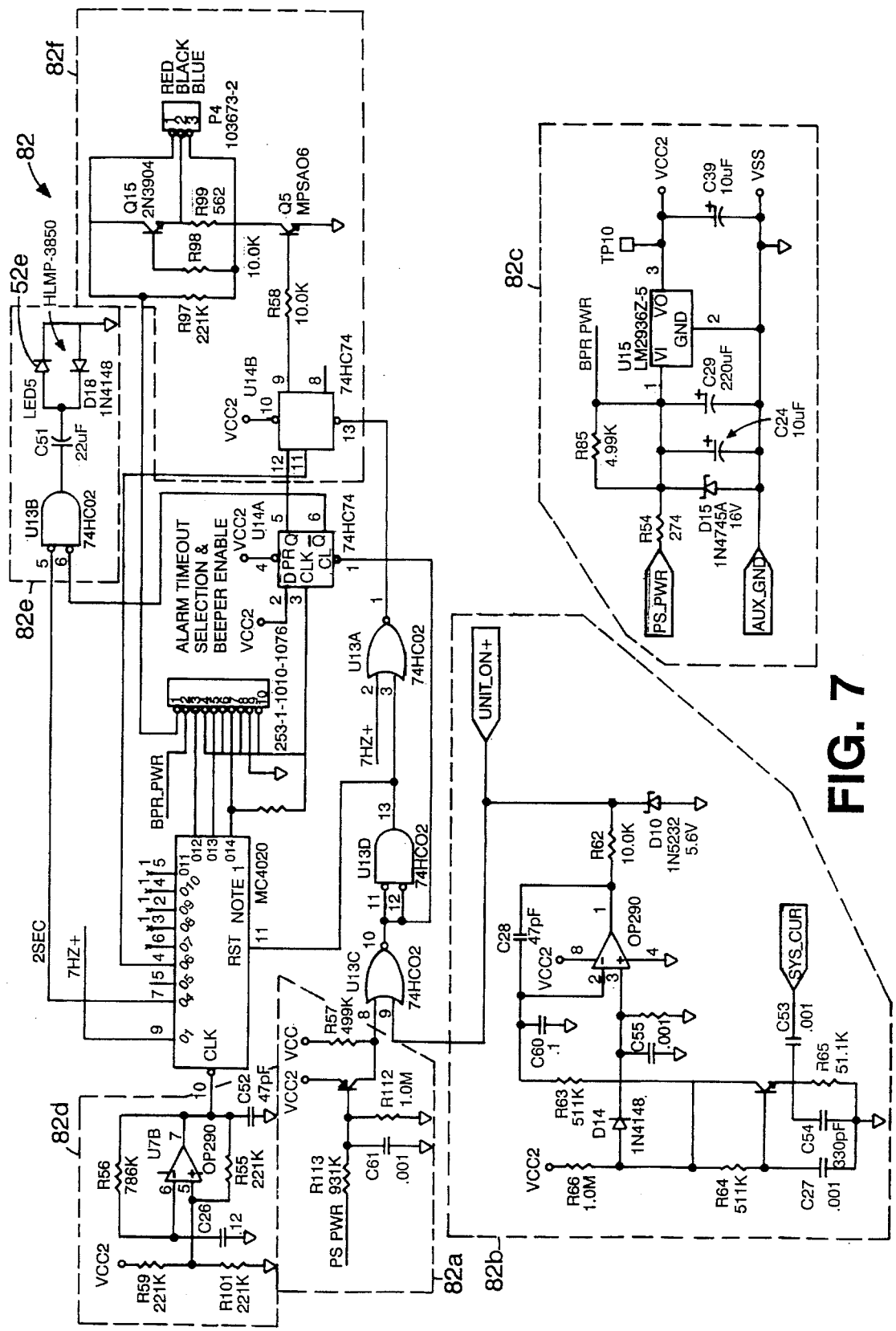
FIG. 7 is a circuit diagram of an AC disconnect alarm circuit of the power supply of FIG. 2.

Referring also to FIG. 7, AC disconnect alarm circuitry 82 includes AC power detection circuitry 82a that determines whether the power supply is connected to a source of AC power and unit on detection circuitry 82b that determines whether the defibrillator is activated.

AC power detection circuitry 82a produces an output signal that has a high value when AC power is present and a low value when AC power is not present. When AC power is present, the output signal equals VCC, a DC supply voltage that is produced from the AC power and is connected to the output signal through a resistor R57. When AC power is not present, the output signal is pulled low by transistor Q21.

Unit on detection circuitry 82b produces an output signal (UNIT_ON+) that has a high value when the defibrillator is activated and a low value when the defibrillator is not activated. Unit on detection circuitry 82b determines whether the defibrillator is activated by detecting a unit on signal (SYS_CUR) produced by the defibrillator when the defibrillator is activated. The unit on signal is a 30 millivolt root-mean-squared triangular signal with a 33 kHZ repetition rate.

The unit on detection circuitry includes a small signal filter/amplifier circuit centered around a transistor Q17 and an op amp U7A. This circuit compares a filtered, averaged value of the input signal SYS_CUR to a filtered, peak value of the input signal, and produces an output having a high value when the input signal has the characteristics described above for the unit on signal.

A single zero/single pole band pass filter is formed by the combination of capacitors C53 and C54 and resistor R65, with the low cutoff frequency for the filter being at approximately 3 kHz and the high cutoff frequency being at approximately 240 kHz. The output of the filter appears across the base of transistor Q17, which is biased partially on by resistors R66 and R64. A capacitor C27 provides rejection of changes to the collector voltage below the range of 300 Hz. The filter output is amplified by transistor Q17, which has a gain (the ratio of resistors R66 and R65) of approximately 20. The amplified signal is then fed into a peak detector circuit formed by the combination of resistor R64 and R103, diode D14 and capacitor C55.

The output of the peak detector circuit is applied as the positive input to an op amp U7A. An averaging circuit comprised of a capacitor C60 and a resistor R63 provides a DC trigger voltage at the negative input of the op amp U7A so that a positive differential voltage, which results from an input signal having a peak value that exceeds its average value, causes the op amp output to go high. A capacitor C28 connected between the op amp's output and its negative input provides a high frequency feedback path. The output of the op amp passes through a resistor R62 to produce the output signal (UNIT_ON+) of unit on detection circuitry 82b. The output signal is connected to electrical ground through a zener diode D10.

The presence of a battery and connection to the defibrillator are not explicitly determined. Instead, the AC disconnect alarm circuitry is powered by the battery of the defibrillator through alarm power circuitry 82c. Thus, if the power supply is not connected to the defibrillator, or there is no battery in the defibrillator, the AC disconnect alarm circuitry will not be powered and no alarm will be produced. Because the AC disconnect alarm circuitry runs off the battery, it is designed to maintain the current drain on the battery at less than 200 micro amps.

Alarm power circuitry 82c includes a low drop-out, low power linear regulator device U15 that reduces the 10.5 volt nominal battery voltage (PS_PWR) to a 5 volt supply voltage (VCC2). A resistor R54 acts as a current limiter to prevent the battery from being drained too quickly if the circuit should fail, a diode D15 provides over-voltage protection by limiting the incoming voltage to 16 volts nominal, and capacitors C24, C29 and C39 provide high frequency noise filtering. The 5 volt supply voltage powers all of the AC disconnect alarm circuitry except for beeper 56, which receives power directly from the battery through a resistor R55.

The frequency at which LED 52e flashes and the time period before beeper 56 is activated are controlled by a free-running, 14 HZ oscillator 82d. Oscillator 82d, which has an approximately 50% duty cycle is constructed around an op amp U7B. The positive input of the op amp is connected to a voltage divider that includes resistors R59 and R101, and is connected to the output of the op amp through a resistor R55. The negative input of the op amp is connected to ground through a capacitor C26, and is connected to the output of the op amp through a resistor R56. The output of the op amp is connected to ground through a capacitor C52 that provides RF interference and static discharge protection.

When the output of the op amp is high, the RC network formed by resistor R56 and capacitor C26 charges the negative input of the op amp to two thirds of VCC2 (3.3 volts). When the negative input reaches this value, it exceeds the voltage at the positive input, which causes the output of the op amp to be driven to ground and thereby causes capacitor C26 to discharge. When the voltage at the negative input of the op amp (i.e., the voltage across capacitor C26) reaches one third of VCC2 (1.7 V), it is less than then the voltage at the positive input, which causes the output of the op amp to be driven high and repeats the cycle.

The output of oscillator 82d is connected as the clock input of a 14 stage ripple counter U19. Counter U19 counts down the 14 HZ oscillator frequency to produce a user selectable alarm delay period of two and a half minutes (012), five minutes (013) or ten minutes, where the period is selected by appropriately placing a jumper in a connector P3. In particular, the two and a half minute period is selected by connecting inputs 3 and 4 of connector P3, the five minute period is selected by connecting inputs 5 and 6 of connector P3, and the ten minute period is selected by connecting inputs 7 and 8 of connector P3. If the jumper is not placed in connector P3, the delay period defaults to ten minutes via a resistor R73 that bypasses connector P3. If the jumper is placed so as to connect inputs 9 and 10, the visible and audible alarms are disabled. The audible alarm may be disabled without disabling the visible alarm by removing a jumper that connects inputs 1 and 2 of connector P3.

The outputs of AC power detection circuitry 82a and unit on detection circuitry 82b are connected to the inputs of a nor gate U13C. The output of the nor gate is connected, through an inverter U13D, to a reset input of counter U19. As such, a high value at either the output of AC power detection circuitry 82a (which indicates that the power supply is connected to AC power) or the output of unit on detection circuitry 82b (which indicates that the defibrillator is activated) will deactivate counter C19 and prevent LED 52e or beeper 56 from being activated.

If the outputs of AC power detection circuitry 82a and unit on detection circuitry 82b are both low, then counter U19 will begin to count. When the selected output stage (012, 013 or 014) goes high, this will cause the clock input of a data flip-flop U14A to go high as well. Because the data input of flip-flop U14A is connected to VCC2, the change in the clock will cause the output of the flip-flop to go high and will thereby enable an LED display circuit 82e and a beeper control circuit 82f. The output of the flip-flop will remain high until the flip-flop is cleared by a low value at the output of NOR gate U13C, which is connected to the clear input of flip-flop U14A (i.e., the output will remain high until the power supply is connected to a source of AC power or the defibrillator is activated).

The inverted output of flip-flop U14A is connected to an input of a NOR gate U13B in LED display circuitry 82e. The other input of NOR gate U13B is connected to an output 04 of counter U19 that transitions about once every 1.1 seconds. When the output of flip-flop U14A is low, the inverted output of flip-flop U14A is high. This causes the output of NOR gate U13B to remain low regardless of the status of counter U19, which thereby deactivates LED 52e.

When the output of flip-flop U14A goes high, the inverted output of flip-flop U14A goes low and the output of NOR gate U13B begins to transition with the output 04 of counter U19. As the output 04 transitions to a low value, the output of NOR gate U13B, which is connected to LED 52e through a series capacitor C51, transitions to a high value. This transition passes through capacitor C51 to produce a spike of current that flows through the LED and illuminates. When the output 04 transitions to a high value, a negative voltage spike is produced and the LED is turned off. Thereafter, the capacitor is discharged by a diode D18. Because output 04 transitions once every 1.1 seconds, LED 52e blinks at a similar rate.

Beeper control circuit 82f sounds beeper 56 once every nine seconds. The output of flip-flop U14A is connected to the data input of a flip-flop U14B in beeper control circuit 82f so that the beeper control circuit is disabled until the output of flip-flop U14A goes high and is thereafter enabled.

The clock input of flip-flop U14B is connected to an output 06 of counter U19 that transitions once every nine seconds. When the output of flip-flop U14A is high and output 06 transitions to a high value, the output of flip-flop U14B, which is connected to the base of a transistor Q5 through a series resistor R58, goes high and turns on transistor Q5. When transistor Q5 is turned on, a beep oscillator circuit that includes resistors R97, R98 and R99, and a transistor Q15 is enabled. If power to the beeper circuit is enabled through inputs 1 and 2 of connector P3, beeper 56, which is connected to the oscillator through a connector P4, is turned on. Approximately 75 milliseconds later, the output of flip-flop U14B is driven low and beeper 56 is turned off so that the audible alarm is a 75 millisecond beep every 9 seconds.

The output of flip-flop U14B is driven low by a signal connected to the clear input of the flip-flop. This signal is produced by a NOR gate U13A having the output of inverter U13D connected to one of its inputs and an output 01 of counter U19 connected to its other input. Output 01 transitions at a frequency of 7 Hz and causes the output of the flip-flop to be driven low after about 75 milliseconds. The output of inverter U13D causes the output of the flip-flop to be driven low when the power supply is connected to a source of AC power or the defibrillator is turned on.

Beeper 56 is a three-leaded piezo type speaker that includes power, ground and feedback connections. The feedback signal is brought to the base of transistor Q15 via resistor R98 to cause the circuit to oscillate at the speaker's resonant frequency (approximately 4700 Hz), and to thereby optimize speaker performance.

Other embodiments are within the following claims.

What is claimed is:

1. A power supply for supplying power from an external power source to a battery-powered medical device for charging a battery of the medical device and operating the medical device, comprising:

an external power connection for bringing external power into the power supply;

a power module connected to receive power from the external power connection and having a power circuit configured to convert power from the external power connection to a form useable by a medical device to which the power supply may be connected;

monitoring circuitry configured to monitor the external power connection to determine whether the external power connection is connected to a source of external power and further configured to determine whether the medical device to which the power supply may be connected is turned on; and alarm circuitry configured to generate an alarm when the monitoring circuitry determines that the external power connection is not connected to a source of external power and that the medical device to which the power supply may be connected is not turned on.

2. The power supply of claim 1, wherein the monitoring circuitry further comprises circuitry configured to determine whether a battery is present in the medical device to which the power supply may be connected, and the alarm circuitry is operable to generate the alarm when the monitoring circuitry determines that the external power connection is not connected to a source of external power, that the medical device to which the power supply may be connected is not turned on, and that a battery is present in the medical device to which the power supply may be connected.

3. The power supply of claim 2, wherein the power supply is configured to be detachable from the medical device to which the power supply may be connected and further comprises:

a housing shaped to conform to a shape of the medical device for attachment to the medical device; and an electrical connector connected to the housing, the connector supplying power from the power supply to the medical device, the connector being located so that it engages a mating electrical connector on the medical device when the power supply is connected to the medical device.

4. The power supply of claim 3, wherein the monitoring circuitry further comprises circuitry configured to determine whether the power supply is connected to the medical device, wherein the alarm circuitry is operable to generate the alarm when the monitoring circuitry determines that the external power connection is not connected to a source of external power, that a battery is present in the medical device, that the medical device is not turned on, and that the power supply is connected to the medical device.

5. The power supply of claim 1, wherein the power supply is configured to be detachable from the medical device to which the power supply may be connected and further comprises:

a housing shaped to conform to a shape of the medical device for attachment to the medical device; and an electrical connector connected to the housing, the connector supplying power from the power supply to the medical device, the connector being located so that it engages a mating electrical connector on the medical device when the power supply is connected to the medical device.

6. The power supply of claim 5, wherein the monitoring circuitry further comprises circuitry configured to monitor the electrical connector to determine whether the power supply is connected to the medical device, wherein the alarm circuitry is operable to generate the alarm when the monitoring circuitry determines that the external power connection is not connected to a source of external power and that the power supply is connected to the medical device.

7. The power supply of claim 1, wherein the power supply is configured to connect to a portable defibrillator and the power circuit is configured to convert power from the external power source to a form useable by the portable defibrillator.

8. The power supply of claim 7, wherein the monitoring circuitry further comprises circuitry configured to determine whether the portable defibrillator is turned on by detecting a signal produced by the portable defibrillator when the portable defibrillator is turned on, and the alarm circuitry is operable to generate the alarm when the monitoring circuitry determines that the external power connection is not connected to a source of external power and the portable defibrillator is not turned on.

9. The power supply of claim 1, wherein the alarm circuitry comprises circuitry configured to produce a visible alarm.

10. The power supply of claim 9, wherein the alarm circuitry comprises an LED and circuitry configured to repeatedly activate and deactivate the LED to produce the visible alarm.

11. The power supply of claim 9, wherein the alarm circuitry further comprises circuitry configured to produce an audible alarm.

12. The power supply of claim 11, wherein the alarm circuitry comprises a disabling component operable to selectively disable the audible alarm.

13. The power supply of claim 12, wherein the disabling component is operable to disable the audible alarm without disabling the visible alarm.

14. The power supply of claim 1, wherein the alarm circuitry is operable to generate the alarm after the monitoring circuitry determines that the external power connection is not connected to a source of external power and a predetermined, selectable delay period has expired.

15. A method of supplying power from an external power source to a battery-powered medical device for charging a battery of the medical device and operating the medical device, comprising:

providing a power supply having an external power connection;

connecting the power supply to a medical device;

bringing external power into the power supply from an external power source through the external power connection;

converting power from the external power source to a form useable by the medical device;

monitoring the external power connection to determine whether the external power connection is connected to the source of external power;

determining whether the medical device is turned on; and generating an alarm when the external power connection is not connected to the external power source and the medical device is not turned on.

16. The method of claim 15, wherein the medical device includes a removable battery, the monitoring step further comprises determining whether a battery is present in the medical device, and the generating step comprises generating the alarm when the monitoring step determines that the external power connection is not connected to a source of external power, that the medical device is not turned on, and that a battery is present in the medical device.

17. The method of claim 16, wherein the power supply is detachable from the medical device, the monitoring step further comprises determining whether the power supply is connected to the medical device, and the generating step comprises generating the alarm when the monitoring step determines that the external power connection is not connected to a source of external power, that a battery is present in the medical device, that the medical device is not turned on, and that the power supply is connected to the medical device.

18. The method of claim 15, wherein the power supply is detachable from the medical device, the monitoring step further comprises determining whether the power supply is connected to the medical device, and the generating step comprises generating the alarm when the monitoring step determines that the external power connection is not connected to a source of external power, that the medical device is not turned on, and that the power supply is connected to the medical device.

19. The method of claim 15, wherein the generating step comprises generating a visible alarm.

20. The method of claim 19, wherein the generating step further comprises generating an audible alarm.

21. The method of claim 15, wherein the generating step comprises generating the alarm after the monitoring step determines that the external power connection is not connected to a source of external power and a predetermined, selectable delay period has expired.

* * * * *